United States Patent [19]

Zytkovicz

[11] Patent Number: 4,467,800
[45] Date of Patent: Aug. 28, 1984

[54] TOOL FOR CREATING A POCKET FOR A EPIDURAL ELECTRODE

[75] Inventor: Duane J. Zytkovicz, Minneapolis, Minn.

[73] Assignee: Medtronic, Inc., Minneapolis, Minn.

[21] Appl. No.: 369,291

[22] Filed: Apr. 16, 1982

[51] Int. Cl.³ .............................................. A61B 10/00
[52] U.S. Cl. .............................. 128/303 R; 128/92 E; 128/305
[58] Field of Search ................... 128/303 R, 305, 304, 128/92 E, 757

[56] References Cited

U.S. PATENT DOCUMENTS

| | | | |
|---|---|---|---|
| 1,533,123 | 4/1923 | Lewis | 128/304 |
| 3,485,236 | 12/1969 | Frost | 128/304 X |
| 4,263,900 | 4/1981 | Nicholson | 128/303 R X |
| 4,349,058 | 9/1982 | Comparetto | 128/305 X |
| 4,372,302 | 2/1983 | Akerlund | 128/303 R X |
| 4,378,811 | 4/1983 | Levitan | 128/304 X |

Primary Examiner—Edward M. Coven
Attorney, Agent, or Firm—Robert J. Klepinski; John L. Rooney; Joseph F. Breimayer

[57] ABSTRACT

A tool having a handle portion and a curved tongue extending from the handle. The curve of the tongue is sufficient that, when the distal end of the tongue is placed substantially parallel to the spinal cord within the epidural space, the proximal portion of the curve extends substantially parallel to the plane passing between spinal vertebrae. The tongue is formed of a pliant material having sufficient rigidity to separate epidural fat to form a pocket in the epidural space, but sufficiently pliant to prevent trauma to the dura and the spine upon contact. A circular disc, having a thickness and width substantially equal to the thickness and width of the electrode to be placed in the pocket, is formed in the distal end of the tongue to shape the pocket to the size of the electrode.

14 Claims, 4 Drawing Figures

TOOL FOR CREATING A POCKET FOR A EPIDURAL ELECTRODE

BACKGROUND OF THE INVENTION

1. Field of the Invention

This invention in general relates to the field of surgical tools, and more particularly concerns a tool that is easily controllable by the surgeon to create a dimensionally proper pocket in the epidural space for the implantation of an epidural electrode, without causing trauma to the tissue of the spinal column contiguous to the epidural space.

2. Description of the Prior Art

Electrical stimulation of the spinal cord has proven to be effective in relieving chronic pain. To provide the stimulation, an electrode at or near the end of a lead is introduced into the epidural space. Generally, the lead attached to the electrode is very small and flexible and thus it is difficult to manipulate the electrode into the epidural space unless a pocket to receive the electrode is created within the epidural fat. Up to now, the tool used to create such a pocket has been a stainless steel strip, approximately 12 inches long by 0.2 inches wide, by approximately 0.02 inches thick made of spring steel. It has been found that this instrument has, at times, caused trauma to the dura and surrounding tissue of the spinal cord. Prior to the present invention, it was thought that necessary stiffness of the tool for creating the pocket, when combined with the great sensitivity of the dura and the tissue surrounding the spinal cord made it practically impossible to avoid at least some degree of trauma when forming this pocket, and it was found that occasionally considerable pain resulted from this procedure.

SUMMARY OF THE INVENTION

It is an object of the invention to provide a tool for creating a pocket for an epidural electrode which greatly reduces the probability and extent of trauma when the pocket is created.

It is a further object of the invention to provide such a tool which overcomes one or more of the disadvantages of the prior art tools.

The invention provides a tool having a handle portion and a curved tongue extending from the handle, the curve of the tongue being along the thinner dimension of the tongue and the curve being of sufficient arc that, when the distal end of the tongue is placed within the epidural space and substantially parallel to the spinal cord, the proximal portion of the curve extends substantially parallel to a plane passing between the spinal vertebrae. A major portion of the tongue is formed of a pliant material having sufficient rigidity to separate epidural fat to form a pocket in the epidural space, but sufficiently pliant to prevent trauma to the dura upon contact. Preferably, the curve is a compound curve with the extreme distal portion of the tongue having a smaller amount of curvature than the portion of the tongue that passes between the vertebrae and into the epidural space. Preferably, the tongue is formed so that it bends more easily at the proximal portion where it joins the handle than at the distal end. Preferably, the pliant material is a material that tends to return to its original shape when released after being deformed, and is a material having a low coefficient of friction with respect to body tissue, preferably of less than 0.2. Preferably, there is a substantially radiopaque means located near the distal end of the tongue so that the position of the distal end may be located by fluoroscopy, and the tongue has a means located off the distal end of the tongue for shaping the pocket to a determined size.

It has been found that the tool as described above creates much less trauma to the spinal tissue than the prior art tools. When the pocket is formed, the dura, if contacted at all will tend to touch only the flat portion of the tool, and if the tip of the tool touches as any portion of the spinal area, it will generally be the bony portion which is much more resistant to trauma. Moreover, it has been found that the tool is much easier to control by the surgeon than previous tools, and thus the pocket formed by the tool is much neater and better holds the electrode. Further, the tool is cheaper to produce than previous tools, making it more cost effective, and disposable, which overcomes resterilization problems that could be encountered with previous tools. Numerous other features, objects and advantages of the invention will become apparerent from the following detailed description when read in conjunction with the accompanying drawing.

DESCRIPTION OF THE PREFERRED EMBODIMENT

Figure 1:
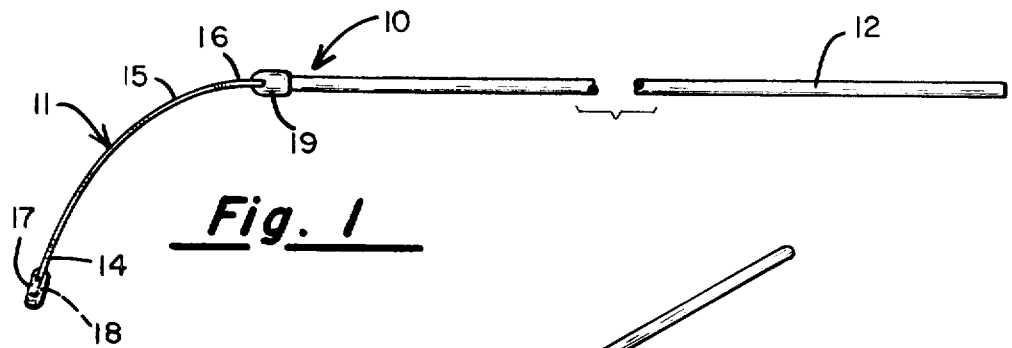
FIG. 1 is a side view of a tool according to the invention.
Figure 2:
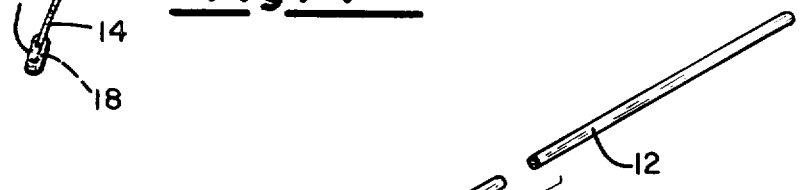
FIG. 2 is a perspective view of the tool of FIG. 1, better showing the broad portion of the tongue.

A side view of a tool 10 according to the invention is shown in FIG. 1 and a perspective view is shown in FIG. 2. The tool includes a tongue portion 11 and a handle portion 12. The tool is used to form a pocket in the fatty tissue of the epidural space 20 (FIGS. 3 and 4) which is the space between the bony portions of the vertebrae 23, 24 and the spinal cord 21.

In the preferred embodiment, the tongue 11 is curved in a compound arc, with the curve being along the thinner dimension of the tongue (the dimension seen in side view in FIG. 1), and with the curvature at the distal end 14 of the tongue being less than the curvature of the portion 15 which extends between the vertebrae and into the epidural space. Preferably the tongue tapers from the distal portion 14 gradually back toward the proximal portion 16. At the extreme distal tip a means 17 for shaping the pocket to a determined size is formed. The means 17 preferably is a circular disc 17 with the thickness of the disc being substantially equal to the thickness of the electrode to be placed in the pocket, and the diameter of the disc being substantially equal to the width of the electrode to be placed in the pocket. Substantially here means sufficiently big that the electrode will fall essentially of its own weight into the pocket with only a small amount of urging by the physician but not so big that the electrode will fit loosely in the pocket. The handle portion 12 of the preferred embodiment is a cylindrical rod and is substantially more rigid than the tongue 11. At the point of connection between the handle 12 and the tongue 11, a barrel-shaped thickened member 19 is formed which has the same diameter as tongue 11 in order to strengthen the tool at the point of juncture.

The preferred embodiment of the tool includes a radiopaque insert 18 in the disc 17 which aids in locating the tip during the formation of the pocket.

Preferably the tool is intricately formed of a material having a good memory, that is, a material that tends to return to its original shape when released after being deformed. Preferably the material is a self-lubricating or wax-like material, that is, it has a low coefficient of friction, and in particular the coefficient of friction between the material and the epidural fat is very low. The coefficient of friction should be preferably less than 0.2 and in the preferred embodiment it is about 0.04.

In the preferred embodiment, the tongue 11 is molded of an acetal homopolymer, such as Delrin TM, produced by DuPont Company of Wilmington, Del., 19898, while the handle is of extruded acetal with the two being joined in a heated mold. The metal insert 18 is preferably of 304 stainless steel.

In the preferred embodiment tongue 11 is 0.045 inches thick and tapers from a width of 0.312 inches at its distal end 14 to a width of about 0.187 at its proximal end 16. Handle 12 is about 0.125 inches in diameter. Disc 17 in this embodiment is of a diameter of about 0.312 inches a thickness of 0.062 inches. Insert 18 is a disc of about 0.15 inches diameter and about 0.02 inches thick.

Figure 3:
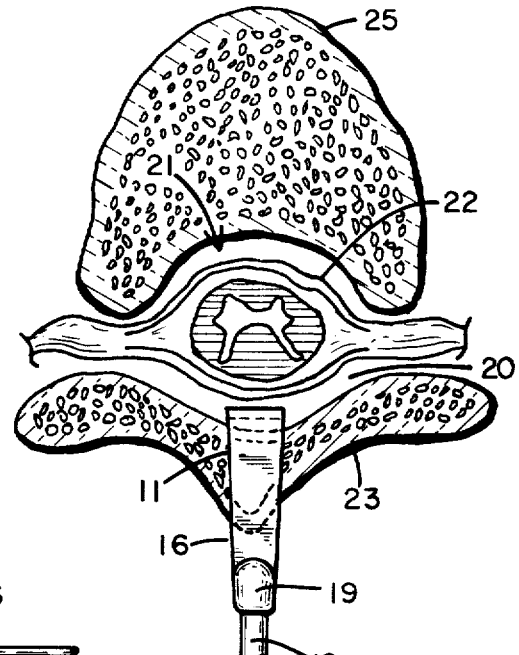
FIG. 3 is a cross-section perpendicular to the axis of the spinal column showing a top view of the tool inserted into the epidural space.

A cross-section through the plane of the spinal column, that is, through a plane perpendicular to the axis of the spinal column is shown in FIG. 3. Such a plane shall be referred to herein as the spinal plane. The spinal column consists of an anterior portion 25 of bony vertebrae and a posterior portion 23 of bony vertebrae with the spinal cord 21 located between them. The sac 22 in which the spinal cord is enclosed is called the dura and the space 20 between the dura 22 and the vertebrae portions 23 and 25 is called the epidural space. The epidural space 20 contains epidural fat and is not a well defined area. It should be understood that there may not be significant separation between the dura 22 and the tissue which covers the surface of vertebrae 23, 25.

Figure 4:
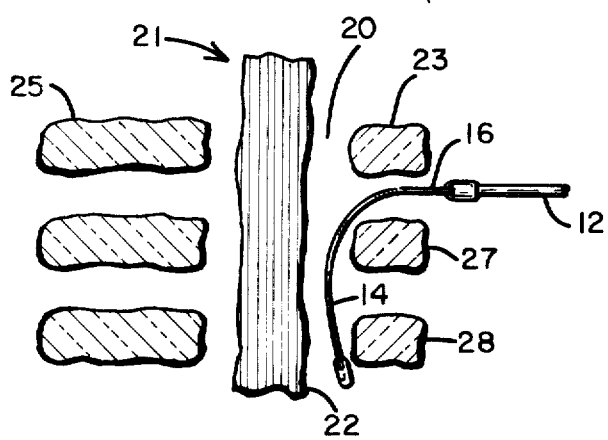
FIG. 4 is a cross-section parallel to the axis of the spinal column showing a side view of the tool inserted into the epidural space.

Because it is near to the surface of the back, the portion of the epidural space between the posterior vertebrae 23 and dura 22 is generally the area in which the lead is placed for spinal cord stimulation. After the vertebral area is exposed in surgery, usually by an open laminectomy, an incision is made in the area in which the lead is to be inserted, and the insertion tool 10 is used to open a pathway between two vertebrae such as 23 and 27 and then under 12 is rotated upward by the surgeon while forcing the tip 17 downward so that it forms a pocket between the vertebrae 27 and 28 and the dura 22 as shown in FIG. 4. At that point, the distal portion 13 of tongue 11 is substantially parallel to the spinal cord while the proximal portion 16 is substantially parallel to the spinal plane, which in this example is the same as the plane between the vertebrae 23 and 17. Substantially is used because, as can be seen from FIG. 4, the position 16 may rotate upward or downward until it just touches the vertebrae and the distal portion can rotate left or right (in the figure) a small distance and still be in the proper region between the vertebrae 28 and the dura 22. The distance between vertebrae 23 and 27 and between vertebrae 28 and dura 22 are larger in the drawing for clarity of illustration, thus these rotations out of the parallel plane as defined by the body parts are quite small in practice.

It is a feature of the invention that, as tongue 11 enters the epidural space and moves downward, any pressure placed against the broad surfaces of the tool, such as 13, will tend to bend it easily rather than cause trauma to the materials exerting pressure on the broad surface such as the dura 22. However, the stiffness of the tip and the pocket-shaping means 18 enables it to easily penetrate the epidural space to form the pocket. Moreover, it has been found that the surgeon, with a little experience with the tool, can easily manipulate tip 17 within the epidural space to precisely locate the pocket for the electrode. This is very important since precise placement of the electrode is crucial in this medical procedure. The radiopaque insert 18 in the tip 17 permits the precise location of the pocket to be determined through fluoroscopy. After the pocket is made the tool slips easily out of the epidural space leaving a pocket for the electrode.

There has been described a novel surgical tool that provides for greatly improved ability to create a pocket in the epidural space for a stimulation electrode while causing minimal trauma to the dura and other tissues in the area, and which can be manipulated easily for accurate location of the pocket by the surgeon. While the invention has been described in connection with a particular embodiment, one skilled in the art will appreciate that numerous other embodiments and departures from the embodiments shown may be made without departing from the inventive concepts. For example, a wide variety of materials may be used for forming the tool, the tongue 11 and handle 12 may be made of different materials or they may be made in a single unit with the handle forming an extension of the tongue, or vice versa. Other shapes of the handle and tongue may be employed within the limits of the broadest claim below. Other features may be added to the tool in addition to the inventive elements. It is therefore to be understood that, within the scope of the appended claim, the invention may be practiced other than as it has been specifically described.

What is claimed is:

1. A tool for creating a pocket for an epidural electrode, said tool having a handle portion and characterized by a curved tongue means extending from said handle, said curve being along the thinner dimension of said tongue and said curve being of sufficient arc that when the distal end of the tongue is placed within the epidural space and substantially parallel to the spinal cord, the proximal portion of the curve extends substantially parallel to the spinal plane a major portion of said tongue being formed of a pliant material having sufficient rigidity to separate epidural fat to form a pocket in the epidural space, but sufficiently pliant to prevent trauma to the dura upon contact.

2. A tool as described in claim 1 wherein said curve is a compound curve.

3. A tool as described in claim 1 wherein said tongue bends more easily near said handle than near the distal end.

4. A tool as described in claim 3 wherein the broad dimension of said tongue tapers gradually from a broader portion near its distal end to a narrower portion near its proximal end.

5. A tool as described in claim 1 wherein said pliant material is material that tends to return to its original shape when released after being deformed.

6. A tool as described in claim 1 wherein said pliant material is wax-like in that it has a coefficient of friction less than 0.2 with respect to body tissue.

7. A tool as described in claim 1 wherein said tongue includes a radiopaque means located near the distal end of said tongue.

8. A tool as described in claim 1 wherein said tongue further comprises a means for shaping said pocket to a determined size.

9. A tool as described in claim 8 wherein said means for shaping comprises a circular disc located at the distal end of said tongue, the thickness and diameter of said disc being substantially equal to the thickness and width respectively of the electrode to be placed in said pocket.

10. A tool for creating an electrode-receiving pocket in an epidural space comprising:
    a handle portion; and
    tongue means mounted on the handle portion for fitting between vertebrae, entering the epidural space, and separating epidural fat to form an electrode-receiving pocket, the tongue means including:
    a flexible proximal portion curved to fit around vertebrae; and
    a pliant wider distal portion having sufficient rigidity to separate epidural fat.

11. The tool of claim 10 wherein:
the proximal portion of the tongue means is more flexible than the distal portion of the tongue means.

12. The tool of claim 11 wherein:
the tongue means tapers gradually from a broad distal end to a narrower proximal end of the proximal portion.

13. The tool of claim 10 further comprising:
a distal end on the distal portion of the tongue means shaped to form the pocket to a predetermined size.

14. The tool of claim 13 wherein:
the distal end includes a circular disc.

* * * * *